United States Patent
Dijkstra et al.

(10) Patent No.: US 10,960,091 B2
(45) Date of Patent: Mar. 30, 2021

(54) SYSTEM AND METHOD FOR STERILIZATION USING ULTRA-VIOLET ILLUMINATION

(71) Applicant: ShenZhen Kaiyan Medical Equipment Co, LTD, Shenzhen (CN)

(72) Inventors: Alain Dijkstra, Amstelveen (NL); Jonathan James Knight, Kent (GB); Jooeun Kim, Seoul (KR); Yong Zhang, Changde (CN); Dan Xu, Shenzhen (CN)

(73) Assignee: FUTUREMEDIX, LLC, Longmont, CO (US)

( * ) Notice: Subject to any disclaimer, the term of this patent is extended or adjusted under 35 U.S.C. 154(b) by 151 days.

(21) Appl. No.: 16/150,130

(22) Filed: Oct. 2, 2018

(65) Prior Publication Data
US 2020/0101183 A1    Apr. 2, 2020

(51) Int. Cl.
*A61L 2/10* (2006.01)
*A61L 2/28* (2006.01)

(52) U.S. Cl.
CPC .. *A61L 2/10* (2013.01); *A61L 2/28* (2013.01)

(58) Field of Classification Search
CPC ..................................... A61L 2/10; A61L 2/28
See application file for complete search history.

(56) References Cited

U.S. PATENT DOCUMENTS

| | | |
|---|---|---|
| 6,656,424 B1 | 12/2003 | Deal |
| 9,517,280 B2 | 12/2016 | Lynn et al. |
| 9,974,873 B2 | 5/2018 | Cole |
| 2017/0246329 A1* | 8/2017 | Lloyd ............... A61L 2/10 |

* cited by examiner

*Primary Examiner* — Sean E Conley
(74) *Attorney, Agent, or Firm* — Emanus, LLC; Willie Jacques

(57) ABSTRACT

The invention provides a UV illumination device for sterilizing and disinfecting a desired item or area. The device is having a built-in camera and UV light source in order to disinfect and sterilize the desired item or area. The device automatically detects the human presence and the acts as a normal household light and can be fit inside the conventional light bulb or tube light holder. Further, the device uses an artificial intelligence module, object detection module, machine learning module, localization module, and a plurality of sensors to easily detect the application area and act according to parameters of a particular item. Furthermore, the device can be manually controlled by using a remote device which is having a display where the user can select, identify, prioritize the items and can adjust the time and intensity of the light projection based upon his/her own intellect.

15 Claims, 8 Drawing Sheets

SYSTEM AND METHOD FOR STERILIZATION USING ULTRA-VIOLET ILLUMINATION

FIELD OF THE INVENTION

The present invention relates generally to a device and method for Ultraviolet (UV) disinfection of physical objects. More specifically, to the device providing UV disinfection or sterilization to a bathroom, hospital room, toilet, door handle and all other areas which need to be sterilized and disinfected with UV radiation.

DESCRIPTION OF THE BACKGROUND ART

Different forms of light can be used in different applications by making use of specific wavelengths of light effects such as, inactivation of bacteria, fungi, viruses, chemical reactions including the curing of plastics and other materials.

Historically, mercury lamps have been the only option for disinfection and sterilization. But with UV LED technology advances, there are new options that are smaller, more robust, toxin-free, long-lived, energy efficient, and allow infinite on/off switching. The UV LED technology allows solutions to be smaller and portable, battery powered, and with the instant full light output.

Ultraviolet (UV) light has been used for many years in the industry, particularly in, health and hygiene regimes.

As known in the art, Ultraviolet (UV) radiation emitted at certain wavelengths is mutagenic to micro-organisms. Sub-type C of the UV spectrum (UVC), also referred as "germicidal" UV radiation, is generally considered to be radiation emitted at a wavelength ranging from 100-280 nanometers. On application, the UVC radiation can be used to inactivate (i.e., destroy, render harmless, and/or prohibit the growth or reproduction) certain micro-organisms.

Prevention of infection by certain micro-organisms is an important concern in places where micro-organisms are substantially present like, laboratory settings, gym, hospitals, locker rooms, and bathrooms etc. In a hospital operating room, for example, it may be important to inactivate microorganisms at the surgical site and on surfaces in the operating room, such as the operating table. This is often accomplished through the use of specialized UV lamp fixtures surface-mounted on the ceiling of the operating room. Also, specialized UV lamp fixtures are often mounted in the ceilings of an operation theatre in hospitals, in order to disinfect the OT apparatuses.

In the U.S. Pat. No. 6,656,424B1 Jeffery L. Deal, discloses an Ultraviolet Area Sterilizer (UVAS) which is mobile or stationary. The UVAS is positioned in a room, such an operating room or intensive care unit. Motion detectors sense movement, to assure that personnel have evacuated the space to be sterilized. Subsequently, UV-C generators, such as a bank of mercury bulbs, generate intense levels of UV-C. An array of multiple UV-C sensors scans the room, and determine the darkest area, or the area reflecting the lowest level of UV-C back to the sensors. A basic Stamp contained in the device calculates the time required to obtain a bactericidal dose of UV-C reflected back from the darkest area. Once a bactericidal dose has been reflected to all the sensors, the unit notifies the operator and shuts down. By relying on reflected doses rather than direct exposure, the UVAS is able to sterilize or sanitize all surfaces within the room that are within view of an exposed wall or ceiling.

In another U.S. Pat. No. 9,517,280B2, William Warren Lynn et. al, discloses a germicidal light fixture and germicidal light fixture system. The germicidal light fixture includes a support structure and at least one first lighting device coupled with the support structure operative to emit ultraviolet radiation at a first predetermined wavelength. At least one second lighting device is coupled with the support structure and is operative to emit ultraviolet radiation at a second predetermined wavelength. The first and second predetermined wavelengths are selected such that ultraviolet radiation emitted from the at least one first lighting device and from the at least one second lighting device, respectively, is operative to inactivate microorganisms. At least one third lighting device is coupled with the support structure and is operative to emit visible radiation.

In another U.S. Pat. No. 9,974,873B2 Theodore John Cole, discloses a germicidal system for use in disinfecting a human interface device includes at least one human interface device. One or more ultra-violet (UV) light sources are used in proximity to the at least one human interface device for disinfecting a touch surface of the human interface device below a surgical grade sterilization. A memory for storing usage data of the at least one UV light source. At least one server is used for providing a central storage location for user data supplied from the memory and a computer is used in communication with the at least one server for controlling the operational parameters of the at least one UV light source.

The existing devices are not compact enough and are only limited to one type of UV radiation which is not effective for complete disinfection and sterilization. The existing devices have multiple parts making the product bulkier and costlier. Further, the existing devices are not capable of object detection and/or material identification for disinfection and sterilization.

Hence, it is desirable to have a device that is smart enough to sense the human presence, identify different materials and provide the UV light projection based on the properties of the different materials.

Further, it is still desirable to have a device which can fit with the existing lighting fixtures and doesn't require any special arrangement for installation.

BRIEF SUMMARY OF THE INVENTION

The present disclosure recognizes and addresses various shortcomings of prior art devices and methods. According to an aspect of the present disclosure, a UV illumination device for sterilizing and disinfecting a desired area or item is described. The device comprises a camera unit, a memory unit, a (UV) light projection unit, and a controlling unit.

According to an aspect of the present disclosure, the camera unit includes a camera and a plurality of sensors. The camera unit is configured to scan at least one item and store a scanned data of the at least one item in the memory unit. Further, the plurality of sensors are adapted to sense the motion and parameters of the at least one item.

The memory unit is adapted to store an information related to the parameters and scanned data of the at least one item scanned from the camera unit. The parameters of the at least one item includes a structure, material, shape, intensity and time required for sterilization and disinfection and other suitable parameters for a particular metal or material.

According to yet another aspect of the present disclosure, the light projection unit includes a light head, a light direction controller, and a UV light source. Further, the UV light source is adapted to project a UV light to the light direction controller which can adjust the direction of the light projection in any desired direction and passes it through the light head.

According to another aspect of the present disclosure, the light direction controller could be a galvanometer, a laser sintering device, a saccade mirror, a direction tuning film or any other device that is able to control the direction of the light projection.

According to yet another aspect of the present disclosure, the controlling unit is operably connected to the camera unit, the memory unit, and the light projection unit. Further, the controlling unit includes a processor which is adapted to execute computer implemented code stored in the memory unit to control the camera unit, the memory unit, and the light projection unit.

Further, the controlling unit is adapted to use an object detection module, localization module machine learning module and artificial intelligence module in order to identify the at least one item within the enclosed area, wherein the enclosed area could be a bathroom, a toilet, an operation theater or any other closed structure needs to be sterilized and disinfected.

According to yet another aspect of the present disclosure, the UV illumination device is adapted to identify the presence of a living organism e.g. a human, an animal, a pet, etc., by using the object detection, localization module, and artificial intelligence and machine learning module. Further, the controlling unit utilizes the camera unit to identify the presence of a living organism. Upon detection of the human presence, the UV Illumination device is adapted to illuminate only the normal light e.g. white household light.

According to yet another aspect of the present disclosure, the memory unit has pre-stored information related to various materials, sizes, shapes, color, texture, etc. to help the UV illumination device to identify the objects and/or materials which needs to be treated with the UV light projection and the objects and/or materials which needs to be prevented from the UV light projection.

According to yet another aspect of the present disclosure, the UV illumination device may be of different shapes and sizes in order to fit in a conventional light bulb holder, a tube light holder and/or a table lamp etc.

According to yet another aspect of the present disclosure, to use the UV illumination device, the user mounts the UV illumination device in the conventional light holder. The UV illumination device is adapted to activate the camera unit to scans the at least one item in the enclosed area and the controlling unit identify the scanned item by using the localization module, the object detection module, the artificial intelligence module, and machine learning module. Further, the controlling unit is adapted to categorize and lists the identified items based on their parameters. Further, the identified items are prioritized based on the frequency of their use. The controlling unit is able to automatically control the intensity, time and shape of the UV light beam based on the parameters of the prioritized item, and projects the UV light beam on the item or object to be disinfected or sterilized.

According to yet another aspect of the present disclosure, the UV illumination device is connected to a remote device via a communication means. The communication means can be a wired or wireless connection between the remote device and the UV illumination device. Further, the UV illumination device may receive user input via the remote device and displays the captured images and videos on the remote device. Further, the user can manually identify, select, prioritize the at least one item to be sterilized and disinfected based upon his/her own intellect by using the remote device. Furthermore, the user can control the shape, time and intensity of the UV light beam based on the parameters of the at least one item by using the remote device.

According to yet another aspect of the present disclosure, the UV illumination device is having a rotation means in order to project the UV illumination in all possible directions. Further, the UV illumination device is compact in size and easily portable.

The foregoing has outlined rather broadly the features and advantages of the present invention in order that the detailed description of the invention that follows may be better understood. Additional features and advantages of embodiments of the invention will be described hereinafter which form the subject of the claims of the invention. The conception and specific embodiment disclosed herein may be readily utilized as a basis for modifying or designing other structures for carrying out the same or similar purposes of the present invention. Please note that such equivalent constructions do not depart from the scope of the invention as set forth in the appended claims. The novel features which are characteristic of the invention, both as to its organization and method of operation, together with further objects and advantages, will be better understood from the following description when considered in connection with the accompanying figures. Each of the figures is provided for the purpose of illustration and description only and is not intended as a limitation of the scope of the present invention or appended claims.

DETAIL DESCRIPTION OF THE DISCLOSURE

Figure 1:
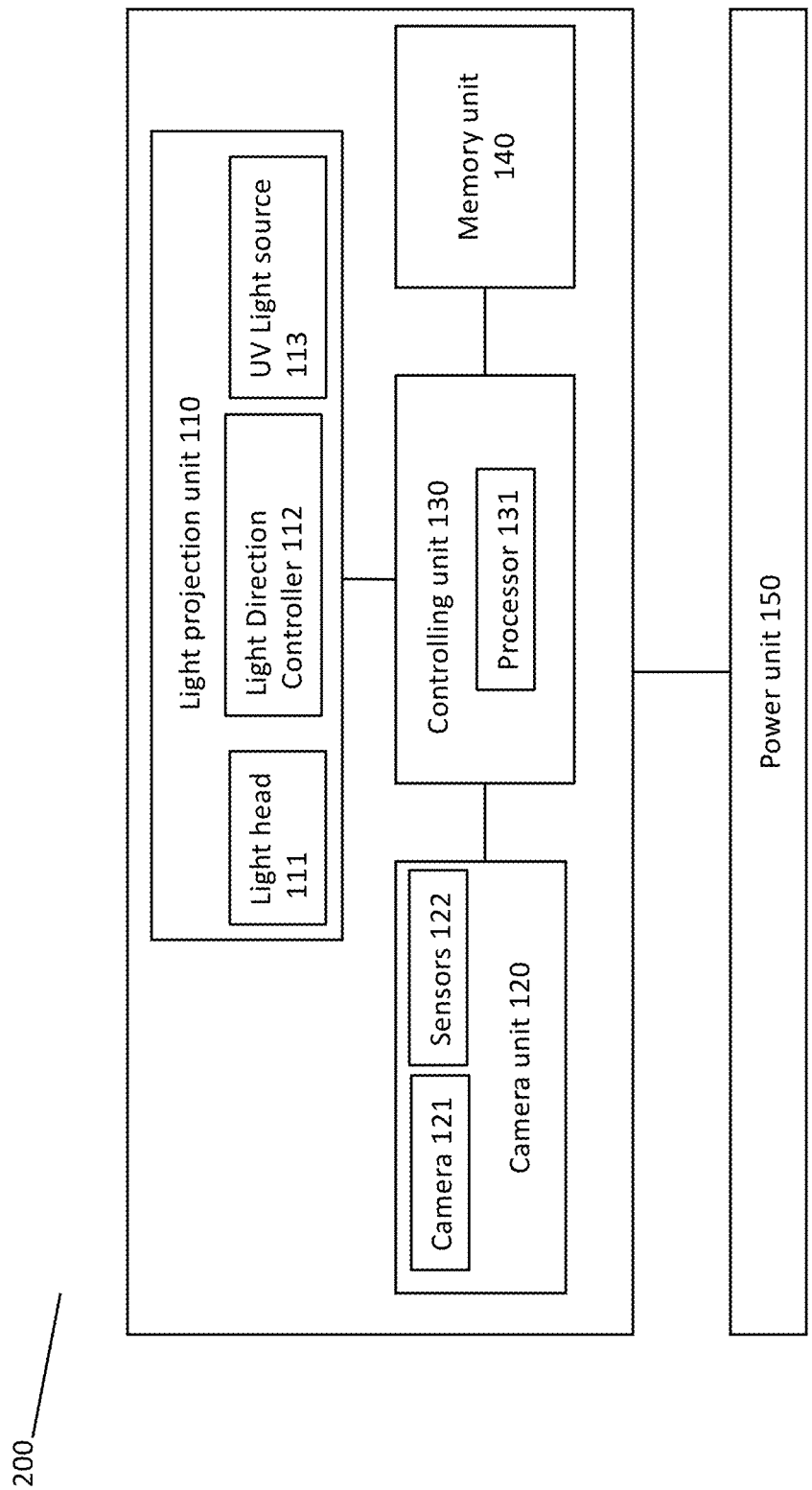
FIG. 1: Shows a block diagram of the components of a UV illumination device according to an embodiment of the present disclosure.

Embodiments of the present disclosure will be described more fully hereinafter with reference to the accompanying drawings in which like numerals represent like elements throughout the figures, and in which example embodiments are shown.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

References to "one embodiment," "an embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an embodiment", "another embodiment," do not necessarily refer to the same embodiment, although they may.

As it is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular, embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A memory unit includes, but is not limited to, a hard drive, compact disc, flash memory, volatile memory, random access memory, magnetic memory, optical memory, semiconductor-based memory, phase change memory, optical memory, periodically refreshed memory, and the like; however, the non-transitory computer readable medium does not include a pure transitory signal per se.

Referring to FIG. 1 shows a block diagram of a UV illumination device 200 according to an embodiment of the present disclosure. The UV illumination device 200 includes a light projection unit 110, a camera unit 120, a controlling unit 130 a memory unit 140 and a power unit 150. Further, the light projection unit 110 includes a light head 111, a light direction controller 112 and a UV light source 113 which is adapted to project the UV light (not shown) on the light direction controller 112, thereafter the light direction controller 112 directs the UV light in the desired direction through the light head 111. Further, the light projection unit 110 also includes a rotation motor that can rotate the light head 111 in any desired direction based upon the controlling unit 130 input.

The UV illumination device 200 uses a mirror galvanometer as the light direction controller. In this, the galvanometer consists of a coil which is suspended by means of silken threads. At least one mirror is attached to at least one coil. The light from the light source is made to fall on one mirror. The reflected light will fall on a light head 111 to project the light on a desired area. When the coil deflects the mirror deflects with it. The light which is deflected also moves on the desired surface. The distance on the desired surface determines the sensitivity of the galvanometer. As the distance increases, the deflection of the light even for a small current will be large. Thus, the even low value can be measured with high precision. Wherein, the light direction controller 112 could use a mirror galvanometer, a laser sintering device, saccade mirror, direction tuning film or any other device that is able to control the direction of the light projection.

The controlling unit 130 is electronically and communicatively coupled to the light projection unit 110, the memory unit 140, the camera unit 120 and the power unit 150. In this, the processor 131 is adapted to control the light projection unit 110 based on the camera unit 120 inputs.

Further, the camera unit 120 includes a camera 121 and a plurality of sensors 122. The camera unit 120 is configured to scan at least one item and store a scanned data of the at least one item in the memory unit 140. Further, the plurality of sensors 122 are adapted to sense the motions of the at least one item and identify parameters of the at least one item, wherein the memory unit 140 includes a pre-stored information related to a structure, material, shape, size, intensity and time required for sterilization and disinfection etc. for a particular metal or material. Further, the controlling unit 130 compares the parameters of the at least one item with the pre-stored information stored in the memory unit 140 to identify the at least one item.

According to an embodiment of the present disclosure, the camera unit 120 is an IP (internet protocol) camera that can rotate in 360-degree angle in order to broaden the scanning area.

Figure 2:
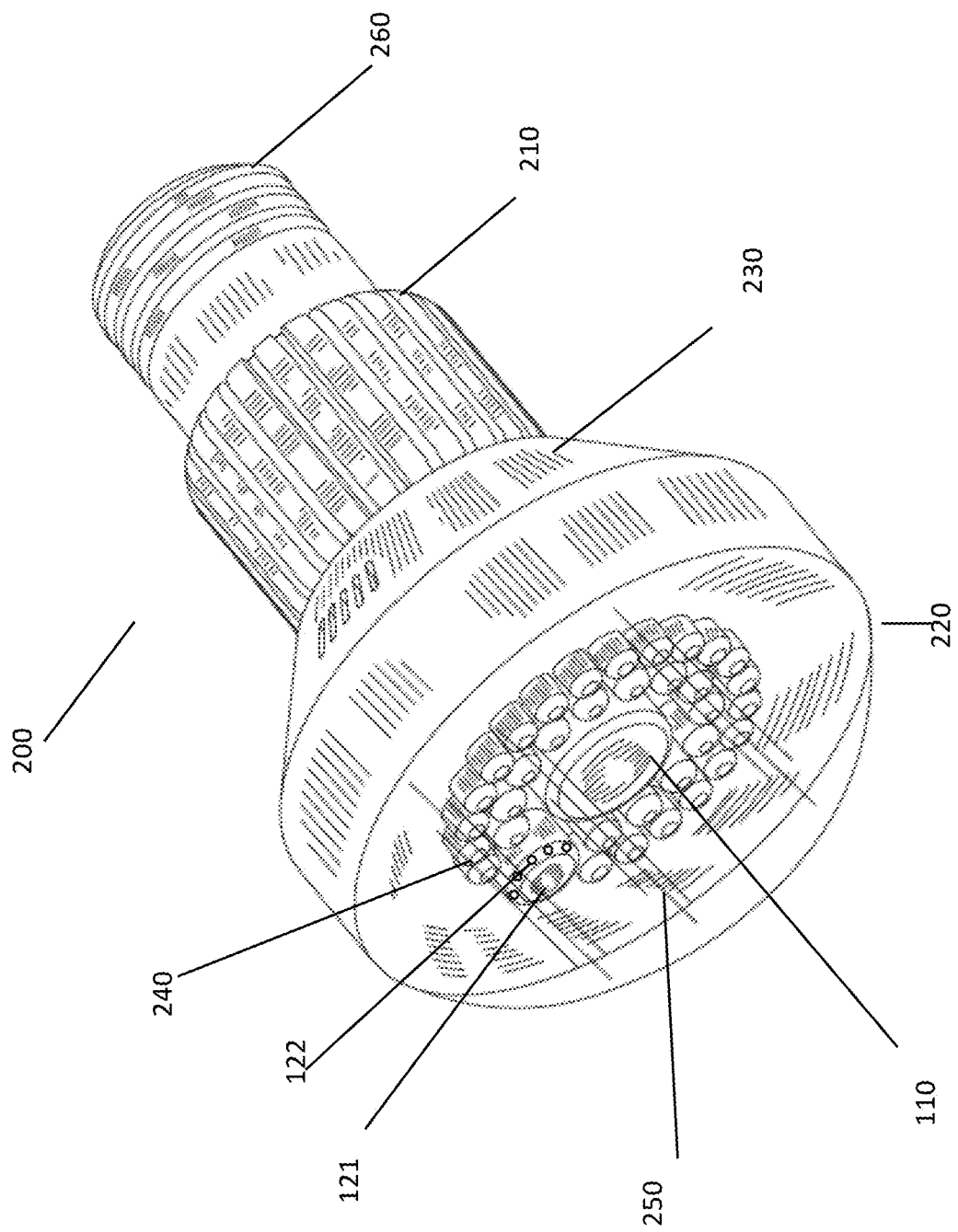
FIG. 2: Shows an isometric view of the UV illumination device according to an embodiment of the present disclosure.
Figure 3:
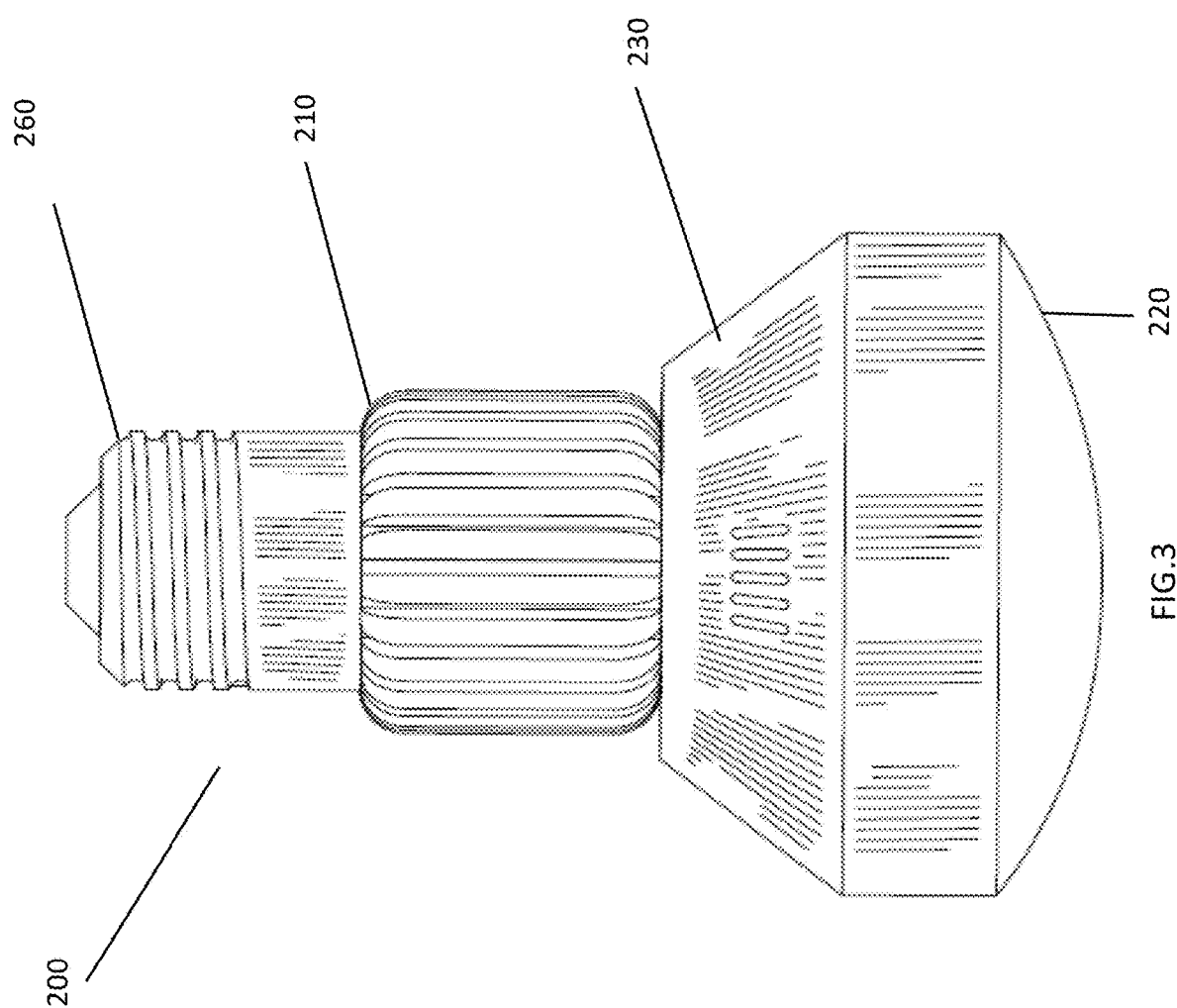
FIG. 3: Shows a plan view of the UV illumination device according to an embodiment of the present disclosure.

Further, the UV illumination device 200 in the shape of a conventional bulb is shown in FIG. 2 and FIG. 3 according to an embodiment of the present disclosure. In this embodiment, the device 200 has a shell body 230 which includes the light projection unit 110 and the camera unit 120. Further, the shell body 230 has a front end 220 and a rear end 210. The front end 220 of the shell body 230 is covered by a transparent cover 250.

The shell body 230 accommodates the light projection unit 110 and the camera unit 120 at the front end 220 and a base 260 is attached at the rear end 210. Further, the light projection unit 110 and the camera unit 120 are substantially encircled by a plurality of LEDs 240 at the front end 220 of the shell body 230. Wherein, the shell body 230 also contains the controlling unit 130 and the memory unit 140 in it.

Further, the light projection unit 110, the camera unit 120, the memory unit 140, the controlling unit 130 and the plurality of LEDs 240 that accommodated within the shell body 230 having an appropriate shape and dimensions, and positive and negative electrical contacts (not shown) to get power from the power unit 150, wherein the power unit 150 can be an external power source or a battery within the UV illumination device 200. Further, when the electrical contacts connect with the power source and the power source is thereby connected to the desired electric parts and accessories. Further, the base 260 has positive and negative terminals to connect the UV illumination device 200 to the external power source.

Figure 4:
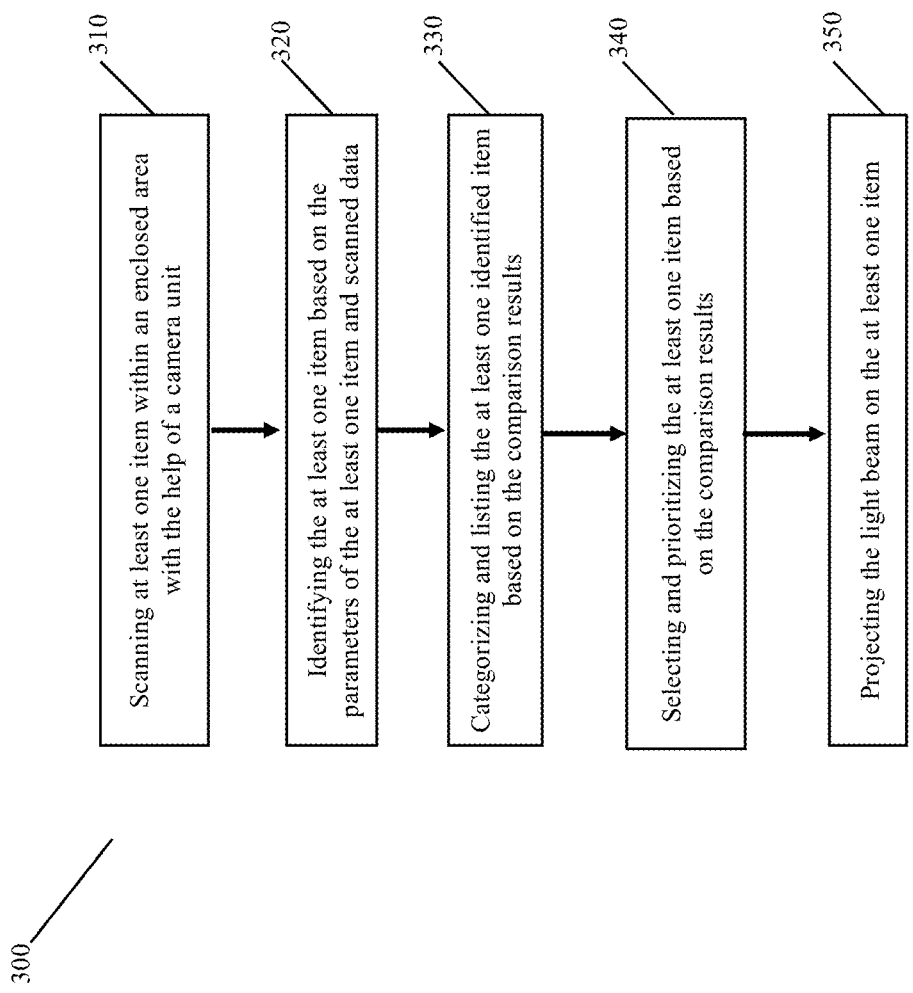
FIG. 4: Show a flowchart of the UV illumination process according to an embodiment of the present disclosure.

Referring to FIG. 4, a flowchart 300 shows the UV illumination process according to an embodiment of the present disclosure, wherein the user switches ON the power supply, thereby activating the controlling unit 130. Thereafter, the controlling unit 130 is adapted to activate the camera unit 120 and direct the camera unit 120 to start scanning an enclosed area to be disinfected or sterilized. The camera 121 scans the at least one item within the enclosed area at step 310, the plurality of sensors 122 collects the parameters of the at least one item. The memory unit 140 receives the parameters of the at least one item and a scanned data from the camera unit 120. At step 320, the controlling unit 130 automatically identifies the at least one item by comparing the parameters of the at least one item and scanned data with the pre-stored information stored in the memory unit 140 by using the artificial intelligence module, localization module, machine learning module and object detection and founds the parameter of the at least one item in the pre-stored information of the memory unit 140. Further, at step 330 the controlling unit 130 categorizes and lists the at least one item based on comparison results. The controlling unit 130 uses artificial intelligence and machine learning module to automatically prioritize and select the at least one item based on the comparisons results at step 340. Furthermore, the controlling unit 130 based on the artificial intelligence and machine learning modules allows the light projection unit 110 to project the UV light beam 114 on the at least one item at step 350. Wherein, if the parameters of the at least one item not found in the pre-stored information of the memory unit 140 the device avoid projecting UV light on the at least one item or a can user via a remote device can manually provide the information to related to the at least one item and the controlling unit 130 allows the light projection unit 110 to project light on the at least one item for a predefined time period and intensity. Wherein the remote device can be a mobile phone, a touchscreen displays, a computer, a laptop, a remote control or any other suitable device allows to view the scanned data and enter user input.

According to an alternate embodiment of the present invention, the user can manually perform the sterilizing and disinfecting operation on the UV illumination device 200. In this, the user establishes a connection between the remote device and the UV illumination device 200 via communication means i.e. wired or wireless connection means. The remote device is having a user interface where the user can see the scanned data from the camera unit 120 and provides input to the controlling unit 130 to scan the enclosed area with the help of the camera unit 120. Further, the user selects the at least one item and categorize the items based on the parameters of the at least one item. After categorizing the items, the user can make a list of the identified and categorized items on the remote device. Thereafter, the user is adapted to prioritize the list based on the frequency of their use and the parameters via using the user interface of the remote device. Further, the remote device sends the prioritized list of the items to the controlling unit 130 and the controlling unit 130 having the processor 131 instructs the light projection unit 110 to project the UV light based on the prioritized list of the items. This is achieved by controlling the UV illumination device 200 via a mobile phone, a mobile application, a laptop, a remote control, an IP controlled camera or any other device which allows a user to identify and select a desired treatment area for the UV illumination.

According to an embodiment of the present disclosure, the controlling unit 130 is having artificial intelligence and machine learning module, localization and object detection module for automatic functioning of the UV illumination device. The controlling unit 130 uses these modules for automatically selecting, identifying, prioritizing various objects or items and provide UV treatment automatically based on the predefined parameters of the object or item.

According to an embodiment of the present disclosure, the localization module provides a complete visual module to localize objects using the camera unit 120. The localization module requires a preprocessing algorithm to segment a scene into objects. Ideally, the preprocessing algorithm should be able to segment an unstructured scene into objects using visual cues such as shape, texture, edges, and color in real-time.

Further, the object detection module provides a way to identify specifically trained objects within the current image. Once the module is trained with sample template images it will identify those objects within the current image depending on the filtered parameters of confidence, size, rotation, etc.

Furthermore, the UV illumination device 200 also uses machine artificial intelligence and learning algorithms to estimate a predictive model that best generalizes to a particular type of data. Therefore, for solving a problem by machine learning and artificial intelligence, it is imperative to have a large number of examples that can be used by the learning algorithm to understand the system's behavior and similar kind of predictions can be generated by the system when the machine learning algorithm is presented with new examples of data. The system records and learns various methods of treatment used by the user or by the UV illumination device 200 for different objects or items. E.g. if a user uses UV light of a particular intensity and shape for sterilizing a particular item the device uses artificial intelligence and machine learning module to learn and recorded all the events happened during the treatment and in future if the UV illumination device 200 is presented with similar item it uses its learning from the previous similar treatment and can automatically provide treatment based on its learning.

Figure 5:
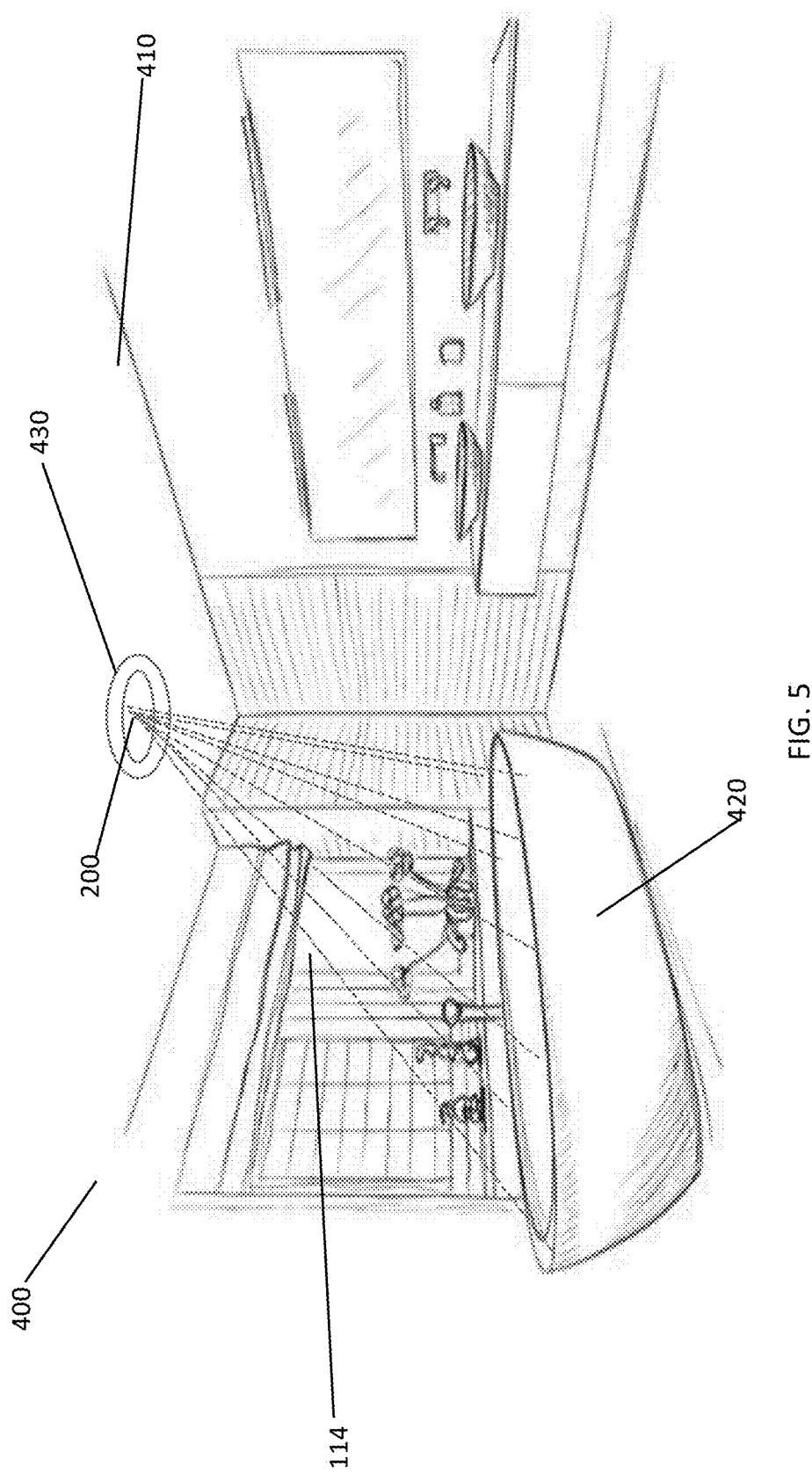
FIG. 5: Shows the configuration of the of the UV illumination device in a bathroom according to an embodiment of the present disclosure.

Referring to FIG. 5, shows the configuration of the UV illumination device 200, in a bathroom 400 according to an embodiment of the present disclosure. In this, the UV illumination device 200 is fixed in a conventional light holder 430 mounted on ceiling 410 of the bathroom 400. The UV illumination device 200 projecting the UV light beam 114 on a bathtub 420 for disinfecting and sterilizing the bathtub 420.

Figure 6:
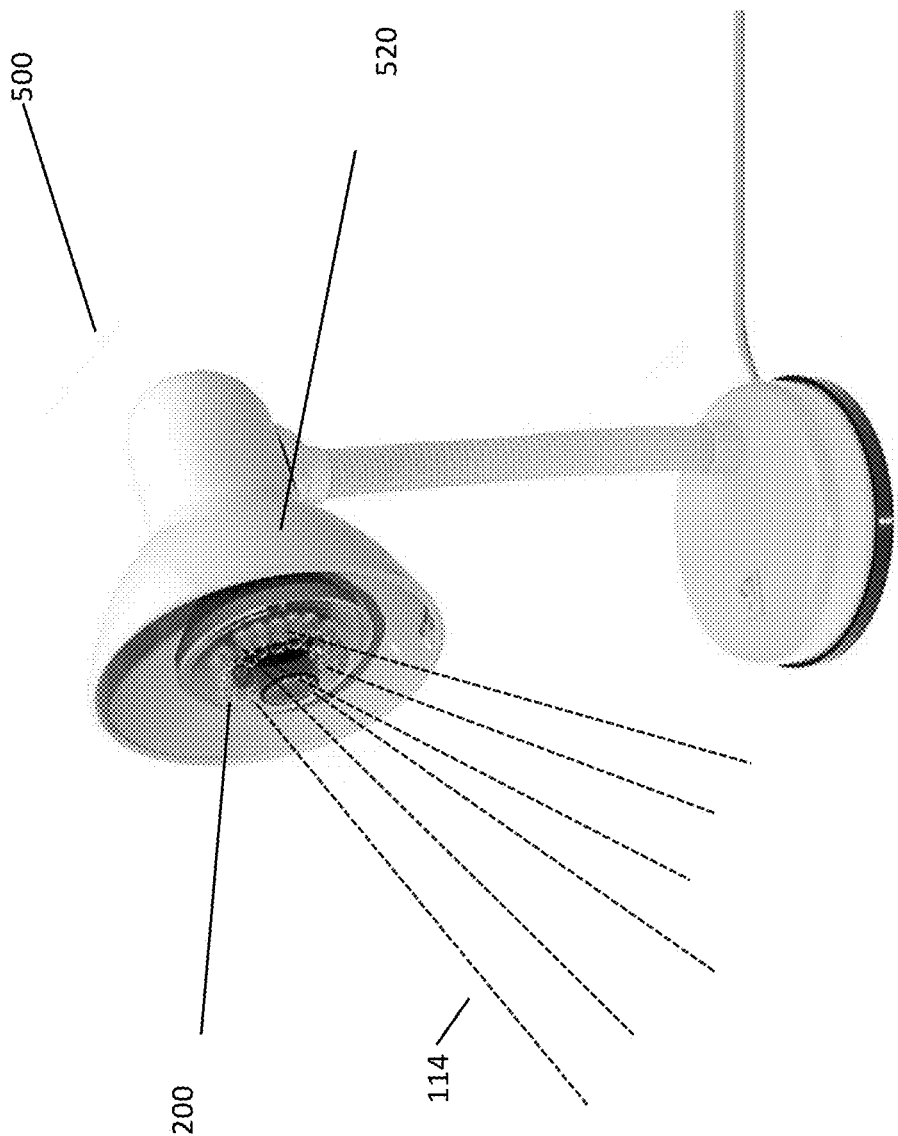
FIG. 6: Shows the configuration of the of the UV illumination device in a lamp fixture according to an embodiment of the present disclosure.

Referring to FIG. 6, shows the configuration of the UV illumination device 200 in a table lamp 500 according to an embodiment of the present disclosure. The UV illumination device 200 is mounted inside a table lamp holder 520 of the table lamp 500 and projecting the UV light beam 114 on the table (not shown).

Figure 7:
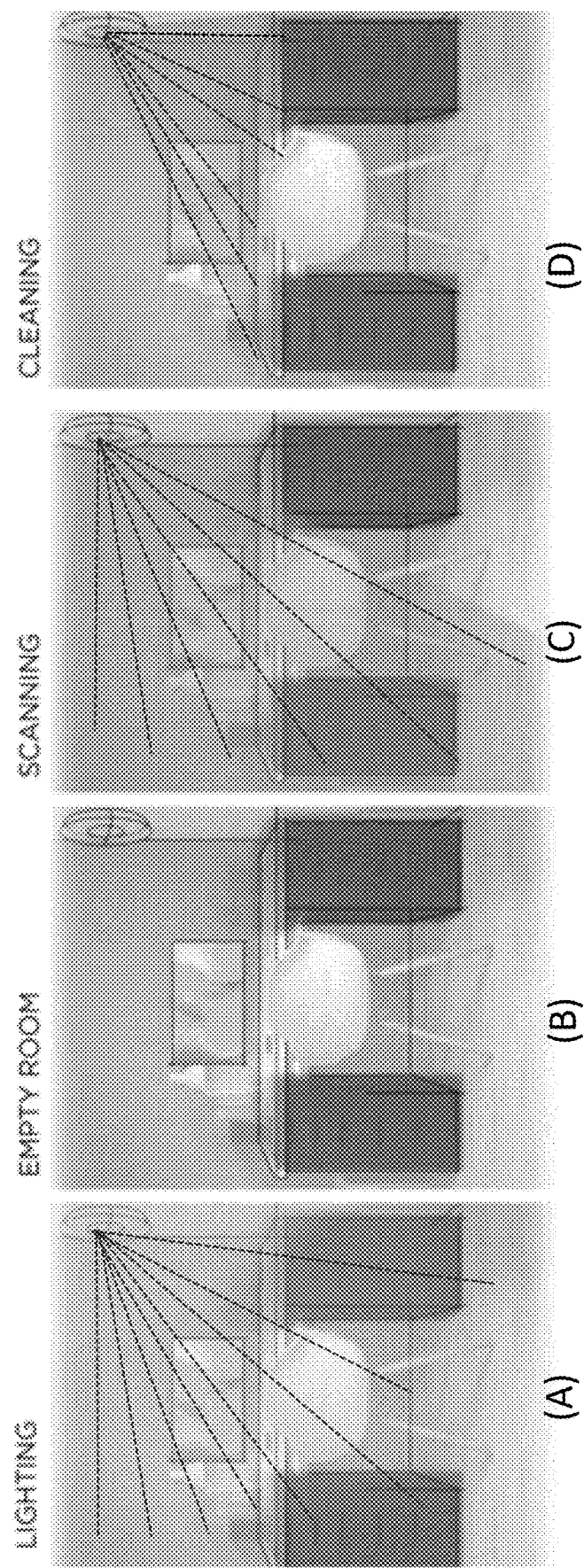
FIG. 7 Shows the various operations performed by the UV illumination device based on the circumstances according to an embodiment of the present disclosure.

Referring to FIG. 7 shows various operations performed by the UV illumination device 200 based on the circumstances in the enclosed area according to an embodiment of the present disclosure. The UV illumination device 200 is mounted on the sidewall of a room. Further, the UV illumination device 200 is responding according to various situations occurring in the room as follows:

According to the situation, 'A', the UV illumination device 200 is illuminating the normal household light. The situation 'A' occurs only when, a person, a pet or any other living organism is present in the room or the door of the room is open.

According to the situation 'B', the UV illumination device 200 is not illuminating any light, this situation occurs when the user just exited the room and the illumination device stops illuminating the normal light.

According to the situation 'C', the UV illumination device 200 is scanning the room and identifying the objects or items which needs to be disinfected or sterilized based on the frequency of their use and their parameters.

According to the situation 'D', the UV illumination device 200 is projecting the UV light on the identified item or object i.e. table as shown in the situation 'D'.

Figure 8:
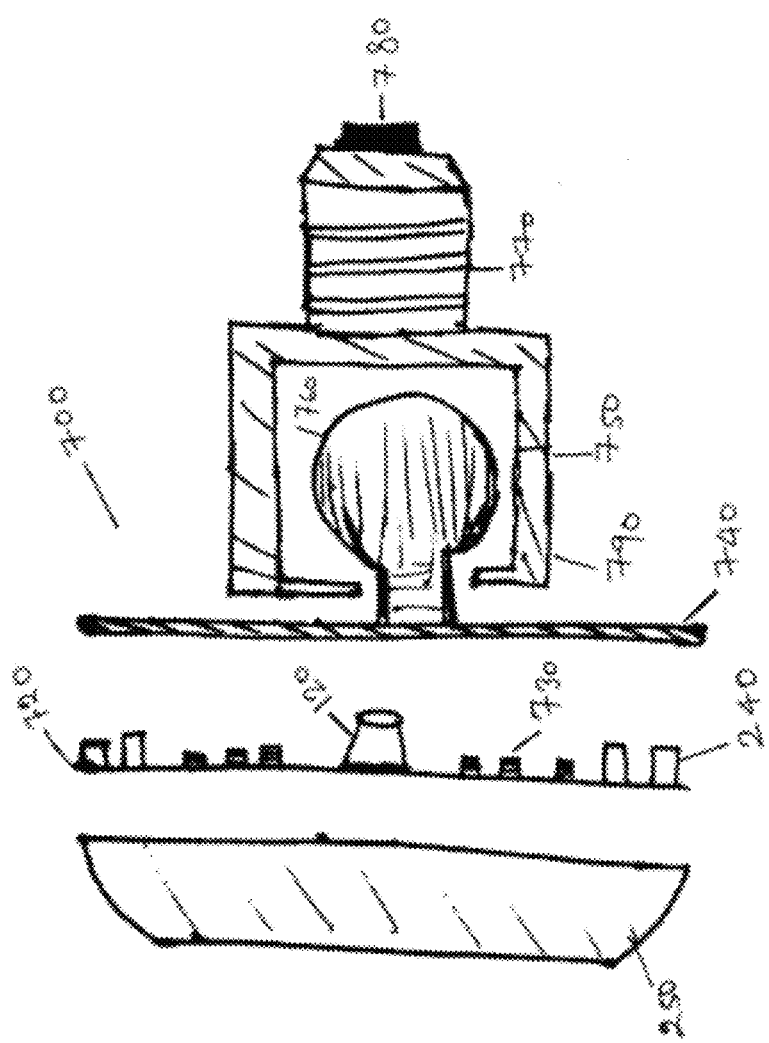
FIG. 8 Shows an exploded view of a UV illumination device according to another embodiment of the present disclosure.

Referring to FIG. 8, an exploded view of a UV illumination device 700 is shown according to another embodiment of the present disclosure. In this embodiment, the plurality of LEDs 240, the camera unit 120, the memory unit 140 (not shown), the controlling unit 130 (not shown) and other required electrical or electronic components 730 are mounted on a base plate 720. The transparent cover 250 is covering the base plate 720 and mounted on a support surface 740, wherein the transparent cover 250 is made of a glass, plastic or any other suitable transparent material. Further, the support surface 740 is attached to a rotation assembly 790 in a rotatable manner, the rotation assembly 790 is a ball socket joint in which a socket 750 is accommodating a ball 760 in a manner that the ball 760 can rotate in any desired direction within the socket 750. Furthermore, a base 770 which is a conventional bulb base is attached to the socket 750 and the base 770 is having electrical terminals 780 in order to establish an electrical connection with the external power source via a conventional bulb holder. Furthermore, the rotation assembly 790 is having a rotation motor (not shown) that is controlled by the controlling unit 130 (not shown) mounted on the base plate 720 in order to rotate the UV illumination device 700 in any desired direction. The controlling unit 130 is using artificial intelligence module, machine learning module, object detection module and localization module to automatically scanning the enclosed area, identifying at least one item, selecting at least one item, prioritizing at least one item, rotating the UV illumination device 700 and illuminating the UV light on the selected and prioritized object or item. The plurality LEDs 240 are acting as UV light source 113 when the UV illumination device 700 starts sterilizing and disinfecting function.

According to an alternate embodiment of the present disclosure, the UV illumination device (200, 700) is having a light source for producing UV light e.g. LEDs, UV lamps, arc welding, laser light, mercury vapors lamps, and all other UV light sources proving light in UV range.

According to an alternate embodiment of the present disclosure, the UV illumination device (200, 700) can use another rotation mechanism e.g. cam mechanism, gear mechanism or any other suitable rotation mechanism.

According to an alternate embodiment of the present disclosure, the enclosed area can be a room, a toilet, an operation theater, a lift or any other desired area to be disinfected and sterilized.

According to an alternate embodiment of the present disclosure, the at least one item within the enclosed area can be a floor, a tub, a door handle, a washbasin, a toothbrush or any other desired item.

According to an alternate embodiment of the present disclosure, the priority of the selected item is decided based on the frequency of the use, in detail the item which is used more often would be more prone to germs hence would be treated first. In this, the device can automatically decide the priority of the treatment or the user can manually decide the priority for the treatment by using a remote device.

According to an alternate embodiment of the present disclosure, the UV illumination device (200, 700) can illuminate the UV light based on the predefined parameter of the object or item to be sterilized or disinfected. The device is able to produce UV-A, UV-B, UV-C, etc. type radiations as per the requirement. Table 1 below describes the various types of UV radiation with their wavelength and property.

TABLE 1

| Name | Abbreviation | Wavelength (nm) | Photon energy (eV, aJ) | Property |
|---|---|---|---|---|
| Ultra Violet-A | UVA | 315-400 | 3.10-3.94 (0.497-0.631) | Long-wave, black light, not absorbed by the ozone layer |

TABLE 1-continued

| Name | Abbreviation | Wavelength (nm) | Photon energy (eV, aJ) | Property |
|---|---|---|---|---|
| Ultra Violet-B | UVB | 280-315 | 3.94-4.43 (0.631-0.710) | Medium-wave, mostly absorbed by the ozone layer |
| Ultra Violet-C | UVC | 100-280 | 4.43-12.4 (0.710-1.987) | Short-wave, germicidal, completely absorbed by the ozone layer and atmosphere |
| Near-Ultra Violet | NUV | 300-400 | 3.10-4.13 (0.497-0.662) | |
| Middle-Ultra Violet | MUV | 200-300 | 4.13-6.20 (0.662-0.993) | |
| Far-Ultra Violet | FUV | 122-200 | 6.20-12.4 (0.993-1.987) | |
| Hydrogen Lyman-alpha | H Lyman-α | 121-122 | 10.16-10.25 (1.628-1.642) | Spectral line at 121.6 nm, 10.20 eV. Ionizing radiation at shorter wavelength |

According to an advantageous embodiment of the present disclosure, the UV illumination device (200, 700) can fit into existing light bulb holder and tube light holder.

According to an advantageous embodiment of the present disclosure, the UV illumination device (200, 700) can automatically sense the human or living organism's presence by using sensors and can act as normal LED light and illuminate light through the plurality of LEDs 240.

According to an advantageous embodiment of the present disclosure, the UV illumination device (200, 700) can automatically detect the microorganisms and items subjected to disinfect and the illuminates UV light corresponding to their parameters.

According to an advantageous embodiment of the present disclosure, the memory unit 140 stores the information of the parameters of the at least one item or object to be sterilize or disinfected e.g. shape, size, structure, material, metal, plastic, intensity and time required for disinfection and sterilization, size and shape of the light beam etc. so that when the camera scan an item the device already have all the information related to that item and the UV illumination device (200, 700) can automatically start the treatment based on the pre-stored information by using an artificial intelligence module, machine learning module and object detection module. Further, in case the UV illumination device (200, 700) doesn't have the information related to the scanned item the user can manually provide the input of the item and the UV illumination device (200, 700) uses machine learning module to store the information provided so that in future the UV illumination device (200, 700) can easily identify the item and can provide the treatment without user intervention.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except in so far as determined by the scope of the appended claims.

We claim:

1. An Ultra-Violet (UV) illumination device used for sterilizing and disinfecting, the device comprising:
   a camera unit;
   a memory unit;
   a light projection unit having a light head for directing at least one UV light beam to a desired area to be sterilized and disinfected;
   a controlling unit connected to the camera unit, the memory unit, and the light projection unit, wherein the controlling unit includes a processor which is adapted to execute computer implemented code stored in the memory unit to perform following steps of:
   scanning, by the camera unit, at least one item within an enclosed area,
   storing, scanned data of the at least one item in the memory unit,
   identifying the at least one item from the scanned data,
   identifying, a presence and/or an absence of a user within the enclosed area and/or an opening in the enclosed area,
   illuminating white household light within the enclosed area, on the identification of the presence of the user and/or the opening, in the enclosed area, and
   projecting the at least one UV light beam on the at least one item identified from the scanned data for a pre-defined time period, on the identification of the absence of the user and/or the opening.

2. The UV illumination device according to claim 1, wherein the UV illumination device includes a UV light source, wherein the UV light source is selected from a group consisting of a light emitting diode (LED), a laser light, and any other light source capable of producing light in UV range.

3. The UV illumination device according to claim 1, wherein the camera unit includes a camera and plurality of sensors.

4. The UV illumination device according to claim 1, wherein the device is configured to utilize an object detection module, a machine learning module, a localization module, and an artificial intelligence module, in order to identify the at least one item.

5. The UV illumination device according to claim 1, wherein the enclosed area is selected from a group consisting of a bathroom, a toilet, a room, a lift, an operation theater, and other closed habitable structures.

6. The UV illumination device according to claim 1, wherein the light projection unit includes a plurality of Light Emitting Diodes (LEDs),
   wherein the plurality of LEDs, the camera unit, the memory unit and the controlling unit have been mounted on a base plate,
   wherein the base plate has been provided on a support surface and has been covered using a transparent cover also mounted on the support surface, and
   wherein the support surface is connected with a base including electrical terminals to establish an electrical connection with an electrical power source.

7. The UV illumination device according to claim 1, wherein the memory unit includes pre-stored information related to parameters of the at least one item, wherein the parameters of the at least one item includes structure, material, shape, intensity and time required for sterilization and disinfection and any other suitable parameters.

8. The UV illumination device according to claim 1, wherein the controlling unit is configured to allow the camera unit to scan the at least one item in the enclosed area and identify the at least one item based on parameters of the at least one item by using a localization module, an object detection module, an artificial intelligence module, and a machine learning module.

9. The UV illumination device according to claim 1, wherein the controlling unit is adapted to categorize and list the at least one item identified based on parameters of the at least one item.

10. The UV illumination device according to claim 1, wherein the controlling unit is adapted to prioritize the at least one item based on the frequency of use of the at least one item, wherein the frequency of use is indicative of susceptibility of the at least one item for contamination by germs.

11. The UV illumination device according to claim 1, wherein the controlling unit is capable of automatically adjust an intensity, shape, and time of the UV light beam based on parameters of the at least one item.

12. The UV illumination device according to claim 1, wherein the UV illumination device is connected to a remote device via a communication means, wherein the remote device is adapted to provide user input to the UV illumination device, and the UV illumination device is adapted to display the scanned data via the remote device.

13. The UV illumination device according to claim 6, wherein the UV illumination device further comprises a rotation assembly including a ball and a socket forming a ball and socket joint between the support surface and the base.

14. The UV illumination device according to claim 1, further configured to receive inputs corresponding to one or more of an identification, a selection, and a prioritization of the at least one item, from a remote device associated with a user.

15. The UV illumination device according to claim 1, further configured to receive inputs corresponding control of shape, time and intensity of the UV light beam based upon parameters of the at least one item, from a remote device associated with a user.

* * * * *